(12) United States Patent
Ettner et al.

(10) Patent No.: US 10,149,799 B2
(45) Date of Patent: Dec. 11, 2018

(54) COMPRESSION TEXTILES

(75) Inventors: Norbert Ettner, Kandern-Wollbach (DE); Andrea Pahmeier, Zossen (DE); Ulrike Kruehner, Diepoldsau (CH); Emilie Bertaux Hegemann, St. Gallen (CH); Florence Mathieu, Estivareilles (FR)

(73) Assignee: SIGVARIS AG, St. Gallen (CH)

( * ) Notice: Subject to any disclaimer, the term of this patent is extended or adjusted under 35 U.S.C. 154(b) by 995 days.

(21) Appl. No.: 13/637,133

(22) PCT Filed: Mar. 23, 2011

(86) PCT No.: PCT/EP2011/054476
§ 371 (c)(1),
(2), (4) Date: Jan. 25, 2013

(87) PCT Pub. No.: WO2011/117310
PCT Pub. Date: Sep. 29, 2011

(65) Prior Publication Data
US 2013/0131563 A1    May 23, 2013

(30) Foreign Application Priority Data
Mar. 25, 2010  (EP) .................................. 10157830

(51) Int. Cl.
| A61H 99/00 | (2006.01) |
| D01F 1/10 | (2006.01) |
| A61F 13/08 | (2006.01) |
| A61F 13/00 | (2006.01) |

(52) U.S. Cl.
CPC ............. *A61H 99/00* (2013.01); *A61F 13/08* (2013.01); *D01F 1/10* (2013.01); *A61F 2013/00931* (2013.01)

(58) Field of Classification Search
CPC ........... A61F 13/08; A61F 2013/00931; A61H 99/00
USPC .......................................................... 601/148
See application file for complete search history.

(56) References Cited

U.S. PATENT DOCUMENTS

| 2,613,520 A | 10/1952 | Schaefer |
| 3,856,008 A | 12/1974 | Fowler et al. |
| 3,889,494 A | 6/1975 | Patience et al. |

(Continued)

FOREIGN PATENT DOCUMENTS

| AT | 008 388 U2 | 7/2006 |
| AT | 507 387 A1 | 4/2010 |

(Continued)

OTHER PUBLICATIONS

The Handbook of Medical Textiles, V. Bartels, Elsevier, Aug. 19, 2011, pp. 167-168.

(Continued)

*Primary Examiner* — Arti Singh-Pandey
(74) *Attorney, Agent, or Firm* — Rothwell, Figg, Ernst & Manbeck, P.C.

(57) ABSTRACT

The present invention relates to a compression textile, e.g. a compression bandage or garment, which comprises at least one chitosan-containing fiber. The compression textile is suitable for medical applications, but also for non-medical applications in the field of wellness and sport.

26 Claims, 9 Drawing Sheets

(56) References Cited

U.S. PATENT DOCUMENTS

| | | | |
|---|---|---|---|
| 5,320,903 A * | 6/1994 | Hirukawa | C08L 1/06 428/326 |
| 5,622,666 A * | 4/1997 | Struszczyk | D01F 1/10 106/166.01 |
| 5,756,111 A * | 5/1998 | Yoshikawa | C08B 37/003 424/402 |
| 5,807,295 A | 9/1998 | Hutcheon et al. | |
| 6,267,744 B1 * | 7/2001 | Roberts | D03D 15/08 602/44 |
| 6,557,274 B2 | 5/2003 | Litchfield et al. | |
| 6,835,678 B2 * | 12/2004 | Jackson | A61L 15/60 15/209.1 |
| 7,007,517 B2 | 3/2006 | Menzies | |
| 7,400,938 B2 | 7/2008 | Ganzoni et al. | |
| 7,441,419 B1 | 10/2008 | Dollyhite et al. | |
| 7,886,776 B2 * | 2/2011 | Jung | A61F 13/00038 139/383 R |
| 2003/0134120 A1 * | 7/2003 | Kim | D06M 15/03 428/375 |
| 2004/0068802 A1 * | 4/2004 | Miller | D06M 13/12 8/115.51 |
| 2005/0189675 A1 * | 9/2005 | Redlinger | C08L 1/02 264/178 F |
| 2006/0021389 A1 | 2/2006 | Menzies | |
| 2006/0085894 A1 | 4/2006 | Yakopson et al. | |
| 2007/0000027 A1 | 1/2007 | Ganzoni et al. | |
| 2007/0033711 A1 | 2/2007 | Achtelstetter | |
| 2007/0042024 A1 | 2/2007 | Gladman et al. | |
| 2007/0283483 A1 * | 12/2007 | Jacober | A41B 11/00 2/239 |
| 2008/0096001 A1 * | 4/2008 | Emden | A41D 31/02 428/222 |
| 2008/0097001 A1 | 4/2008 | Miraftab et al. | |
| 2008/0195016 A1 | 8/2008 | Bottini | |
| 2008/0195019 A1 * | 8/2008 | Ganzoni | A61F 13/00012 602/76 |
| 2009/0181599 A1 * | 7/2009 | Farmer | A41B 17/00 450/39 |
| 2009/0240279 A1 | 9/2009 | Becker et al. | |
| 2010/0055157 A1 * | 3/2010 | Gunn | A61K 33/38 424/447 |
| 2010/0056973 A1 | 3/2010 | Farrow et al. | |
| 2010/0137776 A1 * | 6/2010 | Virkus | A61F 13/08 602/62 |
| 2011/0041232 A1 * | 2/2011 | Covelli | A41D 27/02 2/69 |
| 2011/0212150 A1 | 9/2011 | Redlinger et al. | |
| 2013/0108676 A1 | 5/2013 | Redlinger et al. | |
| 2014/0336020 A1 * | 11/2014 | von Hoffmann | A63B 21/00156 482/124 |

FOREIGN PATENT DOCUMENTS

| | | |
|---|---|---|
| CN | 2684597 Y | 3/2005 |
| CN | 101056551 | 10/2007 |
| CN | 201617188 U | 11/2010 |
| DE | 24 13 332 A1 | 9/1975 |
| DE | 39 16 447 A1 | 11/1989 |
| DE | 602004006851 T2 | 1/2008 |
| EP | 1 759 676 A1 | 3/2007 |
| EP | 1 613 256 B1 | 6/2007 |
| EP | 1 895 036 A1 | 3/2008 |
| EP | 1 700 947 B1 | 8/2009 |
| EP | 2 068 801 B1 | 3/2011 |
| GB | 2 218 638 A | 11/1989 |
| GB | 2218638 | 11/1989 |
| GB | 2260686 A | 4/1993 |
| JP | 10292205 A | 11/1998 |
| KR | 20090039032 A | 4/2009 |
| WO | 98/46818 A1 | 10/1998 |
| WO | 2004/007818 A1 | 1/2004 |
| WO | 2006/032096 A1 | 3/2006 |
| WO | 2006/047153 A1 | 5/2006 |
| WO | 2007112067 A2 | 10/2007 |
| WO | 2008053159 A2 | 5/2008 |
| WO | 2009/092121 A1 | 7/2009 |
| WO | 2009111808 A1 | 9/2009 |
| WO | 2010/031091 A1 | 3/2010 |
| WO | 2010031862 A2 | 3/2010 |
| WO | 2011/117111 A1 | 9/2011 |

OTHER PUBLICATIONS

Beicaro et al.: "Diabetic micro-angiopathy treated with elastic compression", VASA, vol. 19, No. 3, 1990, pp. 247-251.

Armstrong et al.: "Choosing a Practical Screening Instrument to Identify Patients at Risk for Diabetic Foot Ulceration", Archives of Internal Medicine, vol. 158, No. 3, Feb. 9, 1998, pp. 289-292.

Brodovicz et al.: "Reliability and Feasibility of Methods to Quantitatively Assess Peripheral Edema", Clinical Medicine & Research, vol. 7, 2009, pp. 21-31.

Akbari et al.: "Diabetes and peripheral vascular disease", Journal of Vascular Surgery, vol. 30, No. 2, 1999, pp. 373-384.

Dinh: "Review: Peripheral Arterial Disease and Diaetes: A Clinical Update", International Journal of Lower Extermity Wounds, vol. 8, No. 2, Jun. 2009, pp. 75-81.

Eneroth et al.: "Amputation for occusive arterial disease", International Orthopaedics, vol. 16, No. 4, 1992, pp. 383-387.

Young et al.: "The Prediction of Diabetic Neuropathic Foot Ulceration Using Vibration Perception Thresholds: A prospective study", Diabetes Care, vol. 17, No. 6, 1994, pp. 557-560.

Wu et al.: "Foot ulcers in the diabetic patient, prevention and treatment", Vascular Health and Risk Management, vol. 3, No. 1, 2007, pp. 65-76.

Apelqvist et al.: "Prognostic Value of Systolic Ankle and Toe Blood Pressure Levels in Outcome of Diabetic Foot Ulcer", Diabetes Care, vol. 12, No. 6, 1989, pp. 373-378.

Ting et al.: "Clinical and Hemodynamic Outcomes in Patients with Chronic Venous Insufficiency After Oral Micronized Flavonoid Therapy", Vascular and Endovascular Surgery, vol. 35, No. 6, 2001, pp. 443-447.

International Search Report and Written Opinion dated Apr. 20, 2011 issued in PCT/EP2011/054476.

Written Opinion dated Mar. 2, 2012 issued in PCT/EP2011/054476.

International Preliminary Report on Patentability dated Jun. 22, 2012 issued in PCT/EP2011/054476.

Rabe et al.: "Bonner Venenstudie der Deutschen Gesellschaft fuer Phlebologie", Plebologie, vol. 32, Feb. 3, 2003, pp. 1-14.

Abu Rous et al.: "Fluorescent Molecular Probes for the Characterisation of Fibre Structure and Distribution of Textile Resin Finishing on Lyocell", Lenzinger Berichte, vol. 83, 2004, pp. 92-98.

Weder et al.: "X-Ray Tomography Measurements of the Moisture Distribution in Multilayered Clothing Systems", Textile Research Journal, vol. 76, No. 1, 2006, pp. 18-26.

Bartels, Handbook of medical textiles. Elsevier, Aug. 2011, pp. 167-168.

European application No. EP11171910.1, Extended European Search Report dated Sep. 8, 2011, 8 pgs.

International Application No. PCT/EP2012/055217, International Preliminary Report on Patentability dated Sep. 24, 2013, 9 pgs.

International Application No. PCT/EP2012/055217, International Search Report dated Apr. 12, 2012 and Written Opnion, 13 pgs.

U.S. Appl. No. 14/006,707, "Non-Final Office Action", dated Dec. 3, 2015, 9 pgs.

U.S. Appl. No. 14/006,707, "Final Office Action", dated Jul. 6, 2016, 10 pgs.

Definition of "Nonwoven fabric", Retrieved from the internet: http://en.wikipedia.org/wiki/Nonwoven_fabric on May 24, 2016, 7 pages, entry last modified May 11, 2016.

* cited by examiner

COMPRESSION TEXTILES

This application is a 35 U.S.C. 371 National Phase Entry Application from PCT/EP2011/054476, filed Mar. 23, 2011, which claims the benefit of European Patent Application No. 10157830.0 filed Mar. 25, 2010, the disclosure of which is incorporated herein in its entirety by reference.

The present invention relates to a compression textile, e.g. a compression bandage or garment, which comprises at least one chitosan-containing fibre. The compression textile is suitable for medical applications, but also for non-medical applications in the field of wellness and sport.

Medical compression garments (abbreviated by MCG) are garments which are mainly made from elastic knitted fabric. Their aim is to provide a pressure or compressive force, respectively, to a human skin, especially to a limb such as an arm or leg, for e.g. the treatment of venous diseases and lymphatic disorders. Medical compression garments are elastic garments that can, for example, be used to compress a leg below the knee, an entire leg, an arm, a hand and so on. They can be designed as stockings, socks, pants, arm sleeves, gloves etc.

Patients with diseases like the above-mentioned venous diseases and lymphatic disorders are usually required to apply some form of elastic compressive or these during an entire day for a long period of their lifetime and it is therefore desirable to provide an or these in the form of a garment, in particular in the form of a medical compression garment. Patients are generally more compliant with wearing the medical compression garment if it is comfortable to wear. Subsequently, the better the comfort of the used fabric of the garment, the better the treatment compliance can be obtained.

Medical compression garments and their fabrication must comply with normative requirements and specifications such as the German norm RAL-GZ 387/1 or the French norm NF G30-102. These norms impose technical requirements for ensuring medical efficacy of the medical compression garments. Criteria to be checked and requirements to be met are the used materials, the mechanical properties and the physical performance, i.e. the compressive effect of the medical compression garments.

Medical compression garments and methods for their manufacture are e.g. disclosed in EP-A-1 895 036 (Ganzoni Management AG), U.S. Pat. No. 7,400,938 (Ganzoni Management AG), US2007/0000027 (Ganzoni Management AG) and WO2006/047153 (BSN-JOBST INC.), the content of which is herein incorporated by reference.

Compression garments may also be used for non-medical applications such as wellness or sport, e.g. to increase performance and recovery.

Medical bandages are used in place of compression stockings when the limb dimensions are very unusual and standard medical compression stockings cannot fit properly. Medical bandages are e.g. described in EP-A-1 759 676 (Ganzoni Management AG), the content of which is herein incorporated by reference.

There is a need to improve property of compression textiles, e.g. with regard to their bacteriological properties, the wearing compliance and the water-retention properties on the skin.

According to the present invention it was found that textiles comprising a chitosan-containing fibre provide substantial improvements for such parameters.

Chitosan is obtained by deacetylation of chitin, which is a naturally occurring glycan produced in invertebrates, e.g. marine and terrestrial insects, arthropodia or crustaceans as well as funghi. Chitosan is a polycation which can be incorporated into fibres and textiles. The incorporation of chitosan into textile fibres has e.g. been described in WO2004/007818 (Lenzing AG), WO2009/092121 (Lenzing AG) and AT 008388 U2 (Lenzing AG). The content of these documents is herein incorporated by reference.

Thus, in a first aspect, the present invention relates to a compression textile comprising at least one chitosan-containing fibre.

The textiles may be a flat or circular knitted textiles. The knitting construction may be of any known type, e.g. rib, terry loop, float stitch, plain stitch, tuck stitch etc. The textiles may be compression garments, e.g. selected from compression stockings, compression socks, compression leggings, compression arm sleeves (with or without mitten), compression calf sleeves, compression tights, compression gloves, compression tops (T-shirts, long sleeve shirts, tank tops) or compression shorts. These garments are all characterized in that they contain elastic fibres, particularly more than 5%, more particularly more than 15% by weight of elastic fibres.

Further, compression textiles may be stretch bandages, e.g. short stretch bandages (bandages that can be extended by approximately 70% of length by stretching) or long stretch bandages (bandages that can be extended by 150% of length or more by stretching).

The compression textiles may be medical textiles, e.g. textiles for phlebologic or lymphologic applications, textiles for scar formation reduction, or textiles for diabetes patients. Specific applications are anti-thrombosis garments, e.g. leggings or stockings, for use in hospital, textiles for patients with skin traumata, e.g. burn injuries, compression garments, e.g. stockings of class 1, 2, 3 and 4, particularly for patients with dry and/or sensitive skin, e.g. after ulcer treatment. The textiles are also suitable as anti-diabetic stockings, in patients suffering from lymph oedema or for the prophylaxis or treatment of cellulite. It is well-known that patients suffering from diabetes, e.g. diabetes mellitus type 1 or diabetes mellitus type 2 often have oedema, particularly lower extremity oedema.

On the other hand, the textiles of the invention are also suitable for non-medical applications, e.g. for wellness or sport applications.

In some embodiments, the textile may fulfil requirements of national norms, e.g. norms in European countries, for medical compression garments, e.g. stockings. For example, the textile may be in accordance with RAL norm class 1, i.e. a pressure of 18-21 mm Hg (24-28 hPa), class 2, i.e. a pressure of 23-32 mm Hg (31-43 hPa), class 3, i.e. a pressure of 34-46 mm Hg (45-61 hPa) or class 4, i.e. a pressure of at least 49 mm Hg (at least 65 hPa). Further, the textile may be in accordance with AFNOR class 1, i.e. a pressure of 10-15 mm Hg (13-20 hPa), class 2, i.e. a pressure of 15-20 mm Hg (20-27 hPa), class 3, i.e. a pressure of 20-36 mm Hg (27-48 hPa) or class 4, i.e. a pressure of at least 36 mm Hg (at least 48 hPa).

For non-medical, e.g. sport applications, the pressure may be in the range of 5-15 mm Hg (6-20 hPa).

The indicated pressure ranges preferably refer to the pressure at the ankle area.

In case the compression garments, e.g. stockings, are used for patients suffering from diabetes having e.g. lymph oedema, the pressure may be in the range of 10-27 mm Hg, preferably 10-25 mm Hg, at the ankle area.

The pressure values for the textiles may be determined by standard methods, e.g. involving the use of a HOSY meter. For stockings, the pressure values are determined at the ankle level.

The compression textiles of the invention are particularly suitable in persons having sensitive skin, dermatitis, aging skin and/or dry skin. The textiles may be used on injured or undamaged skin.

The textile of the invention comprises at least one chitosan-containing fibre. In a particular embodiment of the present invention, the chitosan-containing fibre is a cellulose-based fibre, e.g. a viscose, modal, polynosic or lyocell fibre, which contains chitosan at least on a part of its surface or a yarn obtained from such a fibre. In a further particular embodiment the chitosan-containing fibre is a cellulose-based fibre, e.g. a viscose, modal, polynosic or lyocell fibre, which contains chitosan only on its surface or a yarn obtained from such a fibre. Such fibres may be prepared by techniques as disclosed in WO2004/007818 or WO2009/092121.

In a preferred embodiment the chitosan-containing fibre is a lyocell fibre coated with chitosan or a yarn obtained from such a fibre. Such a fibre is commercially available as Tencel C from Lenzing AG, for example Tencel C1 and Tencel C2. Generally, the chitosan content of the fibre may be in the range from 0.1-25%, preferably from 0.3-15% by weight based on the total weight of the fibre. In some embodiments, the chitosan content is from 0.3-0.6% by weight and in other embodiments, the chitosan content is from 0.7-1.5% by weight.

The Tencel C fibre (or another chitosan-containing fibre) may be spun to a yarn with a yarn count of Nm20 to Nm225 (dtex 500 to dtex 44), optionally together with other fibres as explained in detail below. The yarns may be ring yarns, compact yarns, OE-roto yarns etc.

Such yarns may comprise 100% Tencel C (or another chitosan-containing fibre) or a mixture (of the chitosan-containing fibre), wherein the amount of chitosan-containing component in the mixture or thread is at least 3%, 10%, 20%, 30%, 40%, 50% or higher based on the total weight of the mixture or thread.

The chitosan-coated fiber or a blend thereof with one or more other fibers may cover an elastic yarn, e.g. a synthetic yarn such as LYCRA™ (spandex, polyurethane fiber), CREORA™ (spandex, polyurethane fiber), ROICA™ (spandex, polyurethane fiber) or DORLASTAN™ (spandex, polyurethane fiber) or any spandex yarn, or a natural elastic yarn such as rubber.

In one embodiment, the compression textile may comprise ply yarns from single ply yarns up to multiple ply yarns and covered ply yarns of 100% Tencel C (or another chitosan-containing fibre) or a mixture or a thread of the chitosan-containing fibre with at least one further fibre with at least one different component, e.g. a component selected from bamboo, wool, cotton, linnen, silk, polyamide, polyester, polyacrylnitrile, polypropylene, viscose, modal and/or micromodal with elastane and/or elastodien, wherein the amount of chitosan-containing component in the mixture or thread is at least 3%, 10%, 20%, 30%, 40%, 50% or higher based on the total weight of the mixture or thread.

In a further embodiment, the compression textile may comprise single and/or double covered yarns for covering an elastic fibre such as elastane or elastodien. These yarns may comprise in 100% Tencel C (or another chitosan-containing component) or a mixture or thread (of the chitosan-containing fibre with at least one further fibre), with at least one different component, e.g. a component selected from bamboo, wool, cotton, linnen, silk, polyamide, polyester, polyacrylnitrile, polypropylene, viscose, modal, micromodal with elastane and/or elastodien, wherein the amount of chitosan-containing component in the mixture or thread is at least 3%, 10%, 20%, 30%, 40%, 50% or higher based on the total weight of the mixture or thread.

In still a further embodiment, the compression textile may comprise core-spun yarns as a wrap spinning for an elastic fibre such as elastane or elastodien. These yarns may comprise 100% Tencel C (or another chitosan-containing component) or a mixture or thread of the chitosan-containing component with at least one different component, e.g. selected from bamboo, wool, cotton, linnen, silk, polyamide, polyester, polyacrylnitrile, polypropylene, viscose, modal, micromodal, elastane and/or elastodien, wherein the amount of chitosan-containing component in the mixture or thread is at least 3%, 10%, 20%, 30%, 40%, 50% or higher based on the total weight of the mixture or thread.

In still a further embodiment, the compression textile may comprise core-yarns as false twist with 100% Tencel C (or another chitosan-containing compound) or a mixture of the chitosan-containing component with at least one different component, e.g. selected from bamboo, wool, cotton, linnen, silk, polyamide, polyester, polyacrylnitrile, polypropylene, viscose, modal, micromodal, elastane and/or elastodien, wherein the amount of chitosan-containing component in the mixture is at least 3%, 10%, 20%, 30%, 40%, 50% or higher based on the total weight of the mixture.

In still a further embodiment, the compression textile may comprise an elasto twist yarn as a wrap spinning for an elastic fibre such as elastane or elastodien. These yarns may comprise 100% Tencel C (or another chitosan component) or a mixture of the chitosan-containing component with at least one different component, e.g. selected from bamboo, wool, cotton, linnen, silk, polyamide, polyester, polyacrylnitrile, polypropylene, viscose, modal, micro- modal with elastane and/or elastodien, wherein the amount of chitosan-containing component in the mixture is at least 3%, 10%, 20%, 30%, 40%, 50% or higher based on the total weight of the mixture.

The compression textiles may comprise unblended chitosan-containing fibres or fibre mixtures of Tencel C (or another chitosan-containing component) in mixtures with other components, such as bamboo, wool, cotton, linnen, silk, polyamide, polyester, polyacrylnitrile, polypropylene, viscose, modal and/or micromodal, wherein the amount of chitosan-containing component in the mixture is at least 3%, 10%, 20%, 30%, 40%, 50% or higher based on the total weight of the mixture.

Suitable knitting techniques for the manufacture of the inventive textiles are flat knitting with one and more needle beds, gauge range E3 to E22, circular knitting, e.g. with one-cylinder hosiery machines and large-scale circular knitting machines, single- and double jersey machines and body- and tubular textile fabric machines.

Suitable knitting constructions are patters with yarns as specified above with Tencel C (or another chitosan-containing component) processed as stitch, inlaid, loop or floating stitch having the following constructions and patterns: right-left, left-left, right-right, rib, imitated rib, floated stitch, jacquard patterns, plated patterns, lace patterns, tuck loop (e.g. micromesh), terry loop, stripe patterns, single- and double jersey.

For example, Tencel C (or another chitosan-containing component) could be used in the understocking of the Sigvaris Ulcer X kit. Indeed, the elastic inlaid yarn of this understocking has a 224 Nm cotton yarn as outer covering yarn (i.e. in contact with the skin of the wearer). The smoothness of Tencel C should also improve the donning thanks to reduction of friction.

The properties of Tencel C also improve healing of the affected skin.

The compression textile according to the invention comprising at least one chitosan-containing fibre thus is also suitably used as an under-article which is in direct contact with the skin. Such "under-articles" are articles, e.g. socks, stockings, knee socks, tights and the like, designed to be slipped on first and thus to be in direct contact with the skin of the patient. Such articles are designed first of all to improve the comfort of the wearer's skin, but can equally advantageously exhibit different properties intended, for example, to yield light support or to reinforce the support action of the main article. In any case, the main innovation of the aforementioned under-articles resides in the fact that they can be more easily slipped on by the user and can provide increased comfort. Suitable under-articles are for example described in EP 1 613 256, the content of which is herein incorporated by reference.

In an especially preferred embodiment, TENCEL™ C (lyocell with chitosan), or another chitosan-containing component, can be used on an inlaid yarn, which may be an elastic fiber such as LYCRA™ (spandex, polyurethane fiber) covered with the chitosan-containing component and optionally further fibers such as polyamide, e.g. PA 6.6. This inlaid yarn may be used together with a loop yarn, e.g. an elastic fiber such as LYCRA™ (spandex, polyurethane fiber),which may be covered with a further fiber, e.g. a polyamide fiber such as PA 6.6. In some embodiments, the loop yarn may also be coated with a chitosan-containing component.

The compression textiles comprising a chitosan-containing fibre have advantageous properties such as:
- antibacterial/bacteriostatic activity, e.g. an improvement of the microbial skin flora,
- high wearing comfort, e.g. smoothness and softness, and compliance, e.g. anti-itching, reduction of skin abrasion and reduction of friction,
- skin moisture management, e.g. water retention, humidity absorption,
- skin thermoregulation,
- skin healing and protection.

In the manufacture of the compression textile it is advantageous that the chitosan-containing fibre (or the chitosan-containing fibre mixture or thread) is in direct skin contact in order to provide high efficacy.

The compression textile may contain the chitosan-containing fibre in its entirety or only in portions thereof. The chitosan-containing fibre may e.g. be present in product parts where there is a particular risk of skin irritation, such as top bands, sewing areas, reverses and/or belts.

In another aspect of the invention, the chitosan-containing fibres as described above such as Tencel C may be used in the form of an above-described compression textile as an agent for treating and/or preventing oedema, particularly tower extremity oedema, in patients suffering from diabetes.

Further, the invention is explained in more detail by the following examples.

EXAMPLE 1

Test for Moisture Regulation In Vitro

The moisture management properties of textile samples were determined by micro computer tomography measurements.

Samples:
Sample 1:
Tubing (19.5 cm. times 10.8 cm) consisting of a loop yarn (LYCRA ™ (spandex, polyurethane fiber) double covered with polyamide 6.6) and an inlaid yarn (LYCRA ™ (spandex, polyurethane fiber) double covered with PA 6.6 and the chitosan-containing fiber TENCEL™ C2(lyocell with chitosan)).

Total components: 34% elastane, 52% PA 6.6, 14% Tencel C2 (based on the total weight).

Sample 2:
Tubing (19.5 cm. times. 10.8 cm) consisting of a loop yarn (LYCRA ™ (spandex, polyurethane fiber) double covered with PA 6.6) and an inlaid yarn (LYCRA ™ (spandex, polyurethane fiber) double covered with PA 6.6 and cotton).

Total components: 34% elastane, 52% PA 6.6, 14% cotton (based on the total weight).

Figure 1:
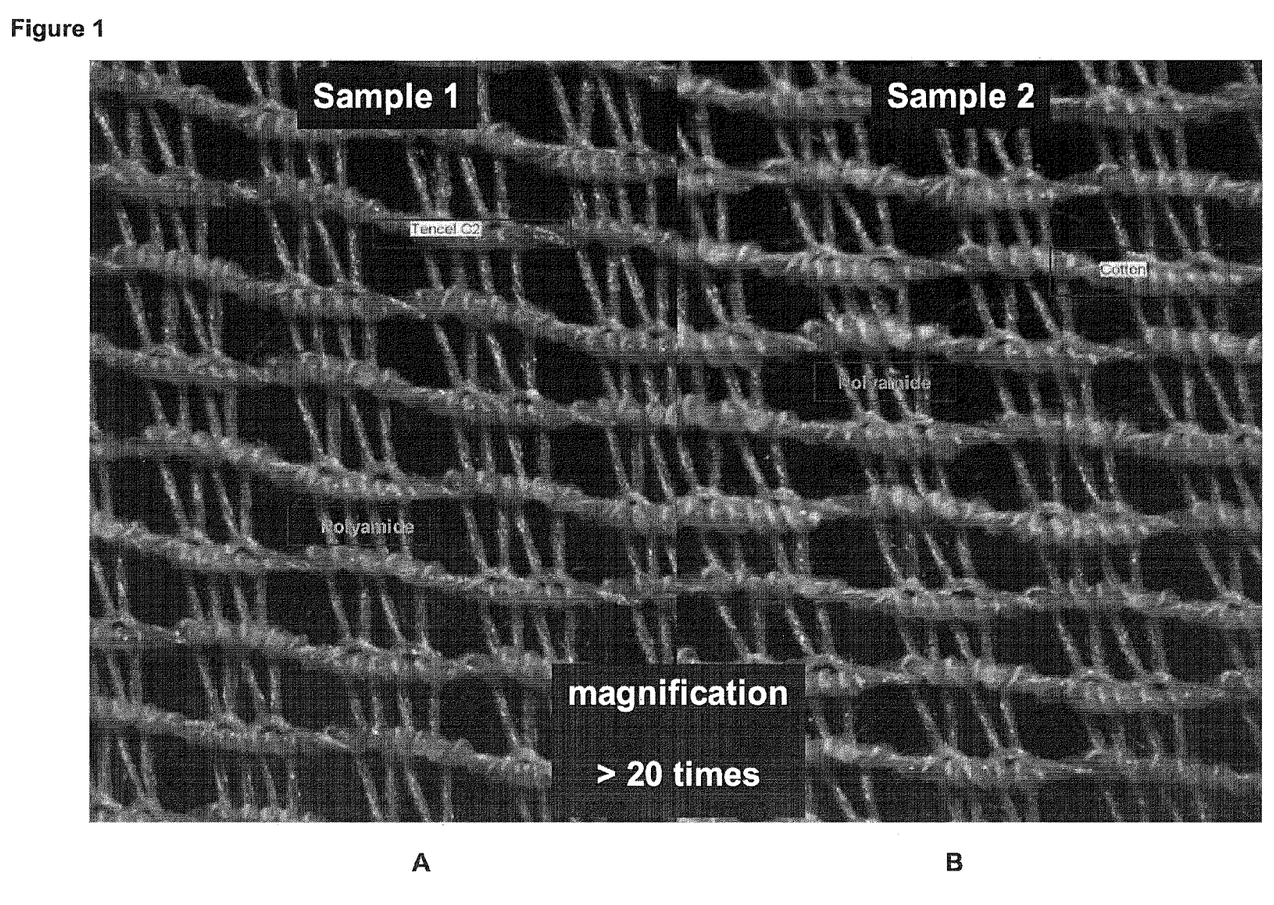

In FIG. 1, microscopic photographs (magnification >20 times) of Sample 1 (A) and Sample 2 (B) are shown. The Tencel C or cotton, respectively, containing inlaid yarns and the polyamide containing loop yarn are indicated.

Test Performance:
Computerised tomography (CT) is a layer-selective radiographic process by which a three-dimensional image can be reconstructed with the aid of a number of sectional photographs corresponding to process one-dimensional projections at different angles. Each projection corresponds to the integration of the attenuation coefficient along the X-ray beam, and by combining the data from different angles, it is possible to reconstruct the two- or three-dimensional image of a sample. The tomograph used is a μCT 80 from Scanco Medical AG, Bassersdorf, Switzerland. The X-ray anode voltage was 55 kV. For objects up to 74 mm in diameter, this device allows one to scan around the object with either 37 or 74 μm resolution, but with different imaging times. The lower resolution was chosen (in all three directions) for faster skin speed to allow a sufficient temporal resolution. A total of 104 projections per 180° were taken and each projection required an X-ray exposure of 200 ms. The two-dimensional detector of the μCT 80 gives 52 slices in a single term, resulting in a image time of 3 min/stack of 50 slices and two stacks were measured per time point, giving a total imaging time of 6 minutes.

The described method is also suitable for representing and quantifying the moisture content in tissues. In order to simulate sweating, the structure according to M. Weder et al., Textile Research Journal, vol. 76(1), 18-26, has been chosen.

The samples were introduced into a holder and adjusted to 35° C.

In order to simulate sweating, water was introduced from a reservoir at two different rates, i.e. 1.25 g/h ("low sweating rate" corresponding to normal activity) and 2.25 g/h ("high sweating rate" corresponding to sport activity).

The measurements were carried out in three phases:
acclimatisation (without sweating)
physical activity (with sweating)
recovery (without sweating)
The results at a low sweating rate are shown in Table 1:

TABLE 1

| | Low sweating rate (a) | |
|---|---|---|
| Sample | 1: made with Tencel C2 | 2: made with cotton |
| Supplied water (g) | 1.28 | 1.28 |
| Outer side (mg) | 45 | 60 |
| Inner side (mg) | 70 | 50 |

TABLE 1-continued

| | Low sweating rate (a) | |
|---|---|---|
| Sample | 1: made with Tencel C2 | 2: made with cotton |
| Total (mg) | 120 | 115 |
| Max water (vol %) | 11 | 11 |

It can be seen that the Tencel C2 containing fibre stores water closer to the skin, i.e. at the inner side of the tubing than cotton. Thus, Tencel C containing fibres provide an increased skin hydration at a low sweating rate.

The results at a higher sweat rate are shown in Table 2:

TABLE 2

| | Higher sweating rate (b) | |
|---|---|---|
| Sample | 1: made with Tencel C2 | 2: made with cotton |
| Supplied water (g) | 2.52 | 2.53 |
| Outer side (mg) | 285 | 340 |
| Inner side (mg) | 235 | 240 |
| Total (mg) | 520 | 580 |
| Max water (vol %) | 52 | 55 |

At a high sweating rate water is sucked away from the inner side and deposited on the outer side for both samples. The skin side is rather dry. Sample 1 (Tencel C) has a lower drying time.

From Tables 1 and 2 it can be gathered that the presence of a chitosan-containing fibre such as Tencel C in a compression textile results in differential moisture regulation properties depending on the sweat rate.

EXAMPLE 2

Test for Moisture Regulation in Human Test Persons

The moisture regulation properties of textile samples were determined by corneometry and tewametry.

Samples:
Sample 1: compression stocking comprising a chitosan fibre, i.e. Tencel C2 (colour white)
Sample 2: compression stocking comprising a cotton fibre (colour beige)

Methodology:
Corneometry

A CM 825 PC Corneometer (Courage+Khazaka, Cologne, Germany) is used to measure the water content.

The face of the sensor is coated with a special glass, which allows axial movement and it has a range of at least 3 mm. The principle of measurement requires that the surface of the measuring device sits evenly at a constant pressure on the skin. To ensure that this is as reproducible as possible, the face of the measuring head is very small with an area of 7×7 mm². The inner movable part—the active face—is pressed onto the skin with a pressure of 3.5 N by means of a spring. This guarantees standardised measurements, irrespective of the investigator.

In order to carry out a measurement, the measuring head is pressed onto the required part of the skin. After one second the measured value is recorded and processed by the computer.

The value measured by the CM 825 Corneometer specifies the degree of moisture of the skin surface.

Tewametry

A Tewameter (Courage+Khazaka, Cologne, Germany) is used for measuring the transepidermal water loss which is a reliable tool for judging the integrity of the skin barrier. The measuring method is based on Fick's law saying that the concentration of water vapour at various distances above a surface is directly related to the quantity evaporated by area and time:

$$dm/dt = -D \times A \times dc/dx$$

dm/dt=diffusion current (water transported per time)
dc/dx=density gradient
D=diffusion constant or water vapour in air
A=surface The most important part of the Tewameter is the probe, consisting of a cylindrical tube, which is open at the top and bottom and which is placed on the surface to be measured. Two capacitive moisture sensors installed in the cylindrical tube measure the moisture of the air at two defined distances above the surface. The water vapour is given in $g/m^2 \times h$. Evaporation rates from 0 to 300 $g/m^2 \times h$ can be recorded by this device.

Test Performance:

The stockings were worn by 31 test persons for 14 days for about 10 hours per day. The stockings were randomly distributed. Each test person wore a cotton stocking on one leg and a Tencel C stocking on the other leg.

Results:

It was found that the chitosan fibre-containing stocking exhibited advantageous properties even after a short time of wear. These advantageous properties were as follows:

In 41% of the test persons the skin showed a marked improvement with Tencel C compared to cotton, e.g. less ragades, wrinkles and hyperkeratoses (in 31% of the test persons there was no difference between both stockings and in 16% of the test persons, the cotton stocking led to skin improvements).

Figure 2:
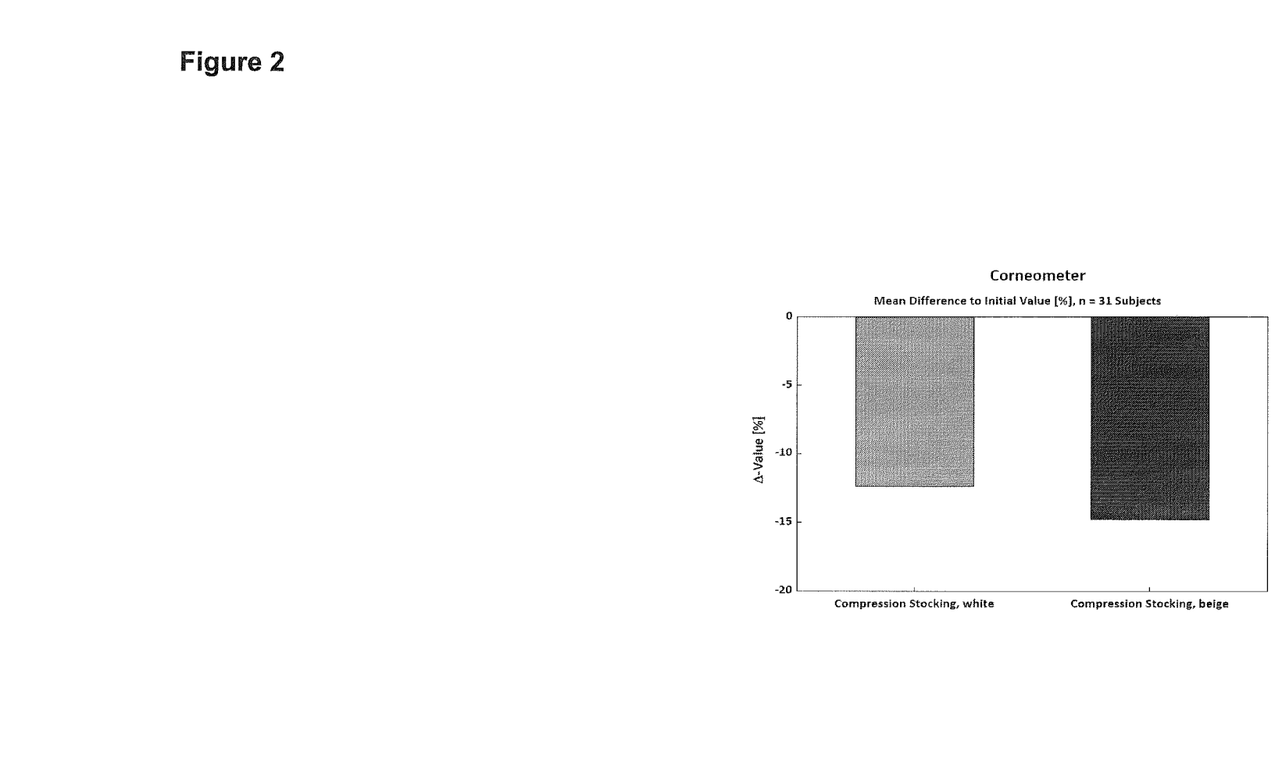

In both stockings, the skin hydration was decreased. The respective results of corneometric measurements are shown in FIG. 2. The decrease in skin hydration for the stocking containing Tencel C, however, was lower (12.4%) than with cotton (14.8%). Thus, Tencel C2 improves skin hydration compared to cotton.

Figure 3:
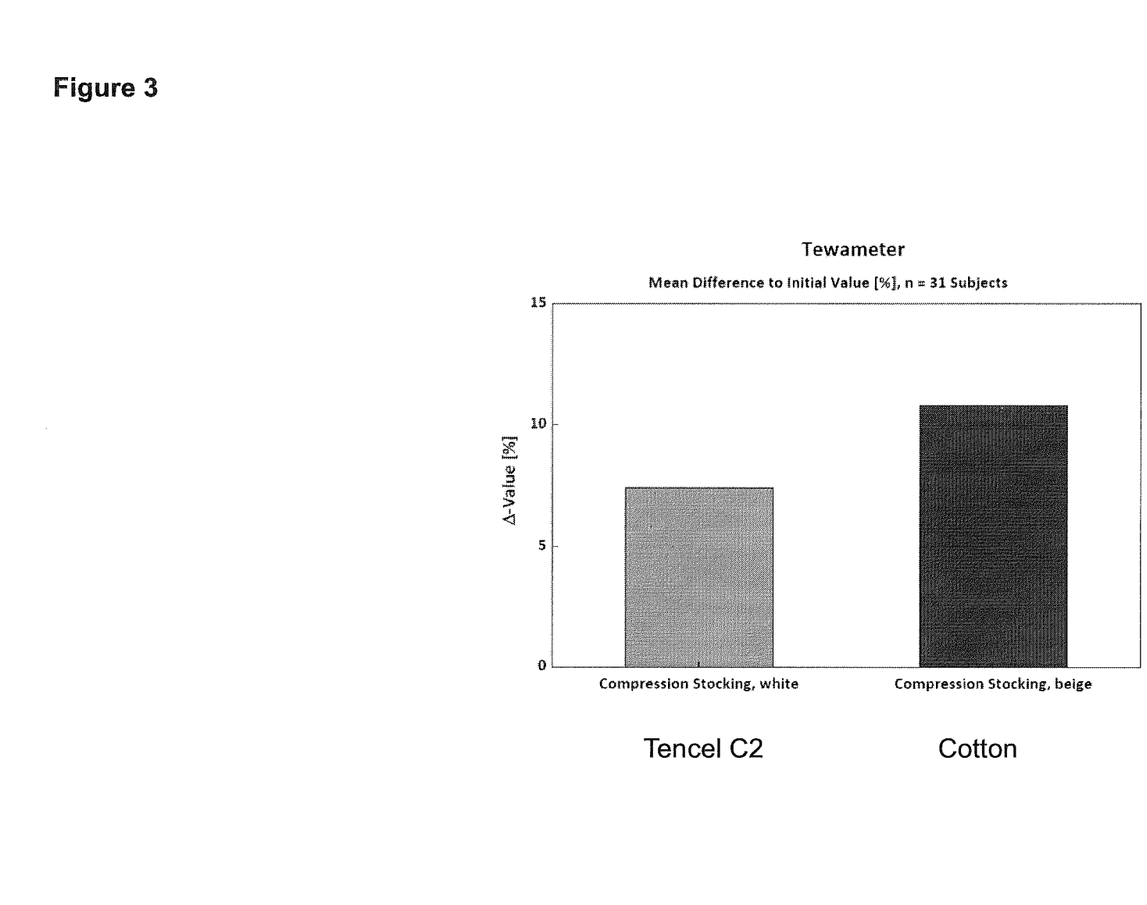

In a further experiment the transepidermal loss of water after removal of the stocking was determined directly on the skin by tewametry. The results are shown in FIG. 3. It can be seen that the transepidermal water loss with the compression stocking containing Tencel C is markedly lower (about 8%) compared to the transepidermal water loss with the compression stocking containing cotton (10.8%). Thus, wearing of a Tencel C containing stocking leads to a decreased water loss of about 0.5 $g/m^2$ skin.

Further, it was found that wearing of compression stockings containing Tencel C leads to a smoothing of skin of about 2% compared to the starting value. The wearing of compression stockings containing cotton did result in a smoothing of the skin.

The results demonstrate that wearing of compression stockings containing Tencel C leads to an improvement in skin quality, particularly higher water retention and higher smoothness of the skin.

EXAMPLE 3

Test for Skin Roughness (FOITS)

The skin roughness was evaluated by fast optical in vivo topometry of human skin (FOITS).

Samples:
Sample 1: Compression stocking comprising Tencel C2 (colour white)
Sample 2: Compression stocking comprising a cotton fibre (colour beige)

Test Performance:

The stockings were worn by 31 test persons for 14 days for a minimum of eight hours per day. The stockings were randomly distributed. Each test person wore cotton stockings on one leg and a Tencel C stocking on the other leg. Creaming of the legs was not allowed one week before the start of the study and during the study.

Methodology:

FOITS is an optical measurement procedure which uses a combination of gray code and phase shift technique (Breuckmann B. (1993), Bildverarbeitung und optische Messtechnik in der industriellen Praxis, Franzis, München). In less than one second, one can measure the absolute space coordinates of all object points in the selected image area with great exactitude. The FOITS-measurement system consists of a projection unit and a CCD camera. Both are fixed under a so-called triangulation angle. Concerning the gray code method, grids with a rectangular brightness distribution by different numbers of lines are projected. The number of lines is doubled at each new projection. This gives a clearly defined hierarchy of lines for each image point. Regarding the phase shift technique, only one grid with a sinus-like intensity distribution is projected several times with different phase positions. A detailed description can be found in Breuckmann B., Bildverarbeitung und optische Messtechnik in der industriellen Praxis, Franzis, München, 1993, and Rohr M., Schrader K. 1998, Fast optical in vivo topometry of human skins (FOITS), SÖFW-Journal 124, 52-59. A CCD camera with a horizontal and vertical resolution in x and y direction of about 30 μm is used. The measurement has been carried out via contactless direct skin measurement of an area of inspection of 1200 mm². The area of measurement (depth-sharpness) was 20 mm. The dissolution in x and y direction was each approx. 30 μm. The dissolution in z direction was 4 μm. The time to digitise the fine structure was about 300 ms.

The roughness parameters Rz and Ra (according to DIN 4768) were determined using twelve separate lines of a length of 20 mm for the analysis.

Rz means average depth of roughness and is the arithmetic means of Rmax in five successive single measuring sections of the total length of measurement.

Ra means the arithmetic mean roughness and specifies the absolute amounts of all variances in the roughness profile from the centreline over the total distance.

Figure 4:
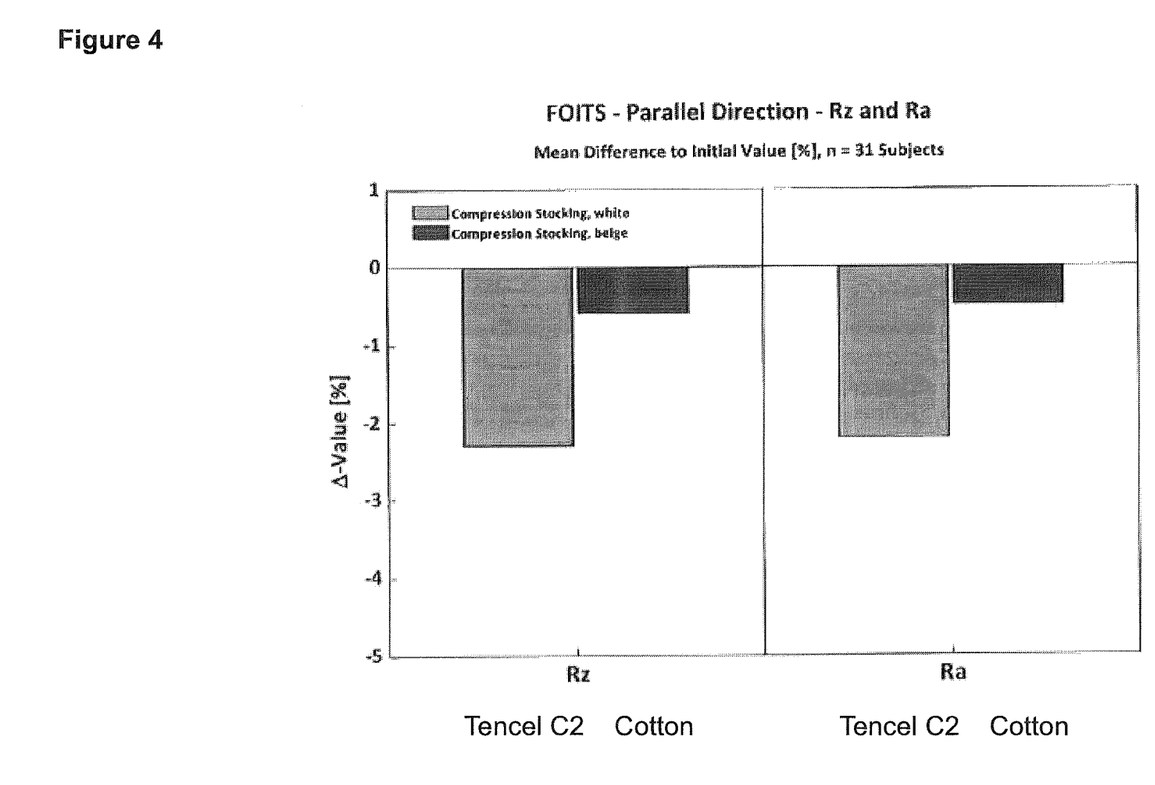

Results:

The results of the skin roughness measurements via FOITS are shown in FIG. 4. Using the Tencel C2 stocking, the average depth of roughness Rz as well as the arithmetic mean roughness Ra showed a difference of about 2.3%-points compared to the starting value, which indicates a reduction of the skin roughness. In case of the cotton stockings, a reduction of the skin roughness of only about 0.5%-points was observed. These results show that Tencel C2 stockings considerably reduce the skin roughness compared to conventional cotton stockings.

EXAMPLE 4

Test for Skin Elasticity

The effects on skin elasticity of the textile samples were determined by cutometry.

Samples:
see Example 3

Test Performance:
see Example 3, except that the study included only 30 test persons.

Methodology:

The Cutometer (Courage and Khazaka, Cologne, Germany) is a vacuum generator with electronic control elements to which the actual measuring probe is connected. Pressure tubing connects the probe and the vacuum generator. The head of the probe is pressed onto the skin. A spring loaded part ensures that constant pressure to the skin is applied.

The displacement of the skin into the probe due to the vacuum is measured optically and transmitted to a PC that is connected to the set-up. The Cutometer sucks an area of skin of approximately 2 mm in diameter in a defined vacuum and then, without friction, optically measures the depth of the skin penetrates into the probe. For a standard test, the instrument generates a vacuum of 300 mbar which is applied to the skin as a sudden jump function. The vacuum is turned off after 5 seconds (on time), also as a sudden jump function and is applied again after another 5 seconds (off time). One measuring cycle is performed in this way.

The standard parameters $R_0$ to $R_7$ can be calculated from the measuring curves. The parameters result from the below calculations.

$R_0$ $R_0$ shows the maximum displacement of the skin after the first suck. It incorporates the elastic stretch of the skin, as well as the plastic portion, which is characterized by a non-linear curve shape.

An improvement in skin firmness is indicated by a decrease of $R_0$.

$R_1$ $R_1$ shows the remaining displacement of the skin when the vacuum has been turned off for five seconds after the first suck. This parameter therefore shows the remaining plastic deformation of the skin after the first suck. It gives information about the ability of the skin to come back in its original state.

$R_2$

The $R_2$ firmness parameter is a combination of $R_0$ and $R_1$.

$$R_2=(R_0-R_1)/R_0$$

This parameter reflects the ratio of the decrease in displacement after the first suck and the total displacement in the first suck (Gross Elasticity).

The greater $R_2$ is, the less plastic deformation remains.

$R_3$ $R_3$ reflects the maximum displacement of the skin after the last suck. It, therefore, incorporates an additional effect compared with $R_0$, namely a wear effect caused by repeated displacement of the skin.

This parameter equals $R_0$ if the measuring cycle is carried out only once.

$R_4$ $R_4$ reflects the remaining displacement after the last suck, and therefore corresponds to $R_1$ plus the wear effect from repeated suction. $R_4$ equals $R_1$ if one measuring cycle is done.

$R_5$

The $R_5$ parameter (Net Elasticity) reflects the elastic portions of the first curve.

$$R_5=U_R/U_E$$

$R_5$ comprises UE, the linear proportion of the first curve, and UR, the linear decrease when the vacuum has been turned off after the first suck. The closer $R_5$ to 1 (100%), the more elastic the skin is.

$R_6$ $$R_6 = U_v/U_E$$

Here UV is the plastic portion of the first curve. $R_6$, therefore, represents the inelastic portion of stretch versus the elastic portion of stretch in the first curve. The higher $R_6$, the more plastic the skin. The lower $R_6$, the more elastic the skin.

$R_7$

Parameter $R_7$ represents a kind of spontaneous elasticity. Namely, the elastic portion after the vacuum has been turned off for the first time is related to the total displacement of the first suck. The closer $R_7$ to 1 (100%) the more elastic the skin. The lower $R_7$, the more inelastic the skin.

$$R_7 = U_R/U_0$$

In this study, parameter $R_0$, $R_1$, $R_2$, $R_5$ and $R_7$ are analysed on a statistical basis. A positive product effect is documented by a decrease of parameter $R_0$ and $R_1$ and an increase of parameter $R_2$, $R_5$ and $R_7$.

Figure 5:
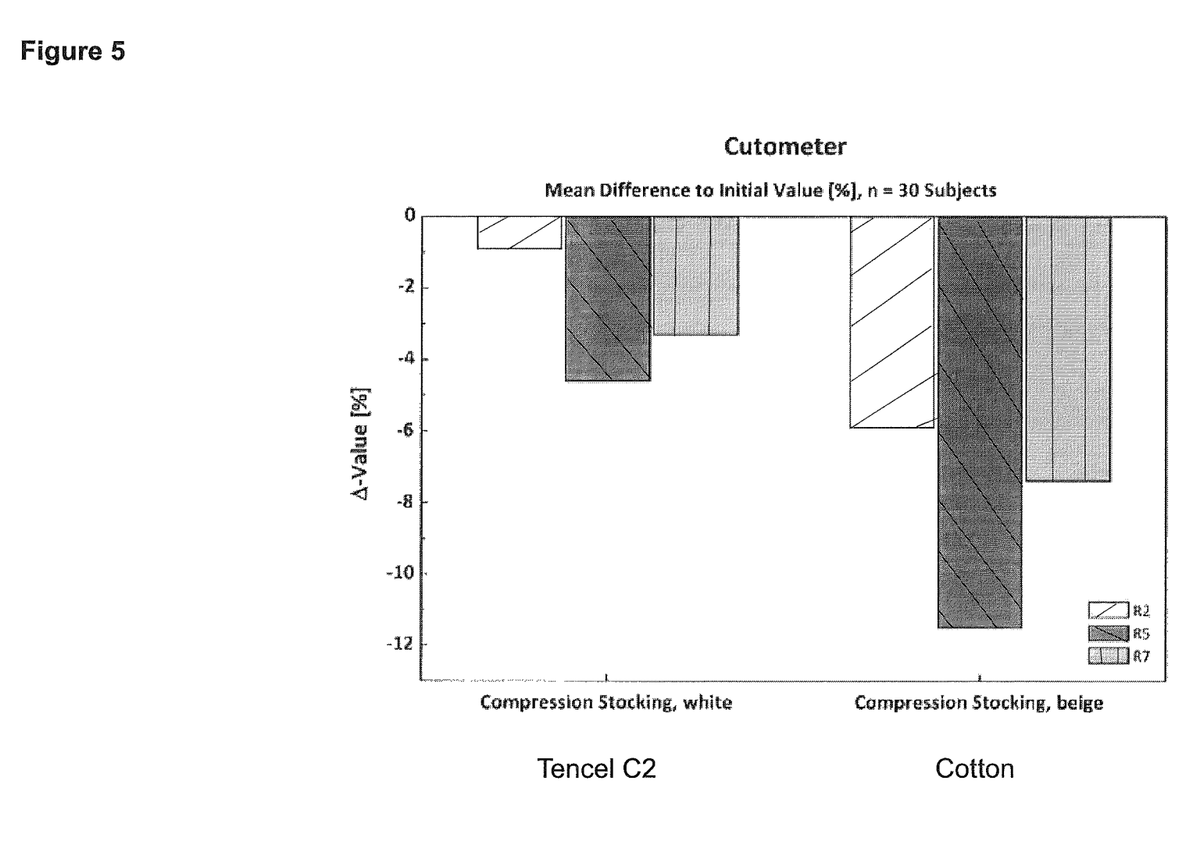

Results:

In FIG. 5, the results of the Cutometry measurements are shown. In all experiments, the values of the parameters $R_2$, $R_5$ and $R_7$ are reduced compared to the starting value. As can be seen from the legs treated with Tencel C2, the $R_2$, $R_5$ and $R_7$ parameters only varied slightly with respect to their starting value as compared to the experiments done with cotton-treated legs. These results show that the Tencel C2 stockings almost maintain the skin elasticity during wearing, whereas skin elasticity is markedly reduced when wearing conventional cotton stockings. Thus, using Tencel C2 stockings, a higher skin elasticity can be maintained as it is the case when using cotton stockings.

EXAMPLE 5

Test for Skin pH

The skin pH value was determined by a pH meter.

Samples:
see Example 3

Test Performance:
see Example 3

Methodology:

The skin pH meter pH 905 (Courage and Khazaka, Cologne, Germany) is used for pH measurements directly on the skin surface. Due to the excretions of skin, skin surface represents almost an aqueous solution. The measurement of skin pH is performed with a glass electrode that reacts on the activity of [H+] ions. The potential of the glass electrode is linearly dependent on the pH value of the measuring solution.

The pH value of healthy skin is about 4.4 to 5.5 at room temperature (20° C. and 40-60% air humidity).

Figure 6:
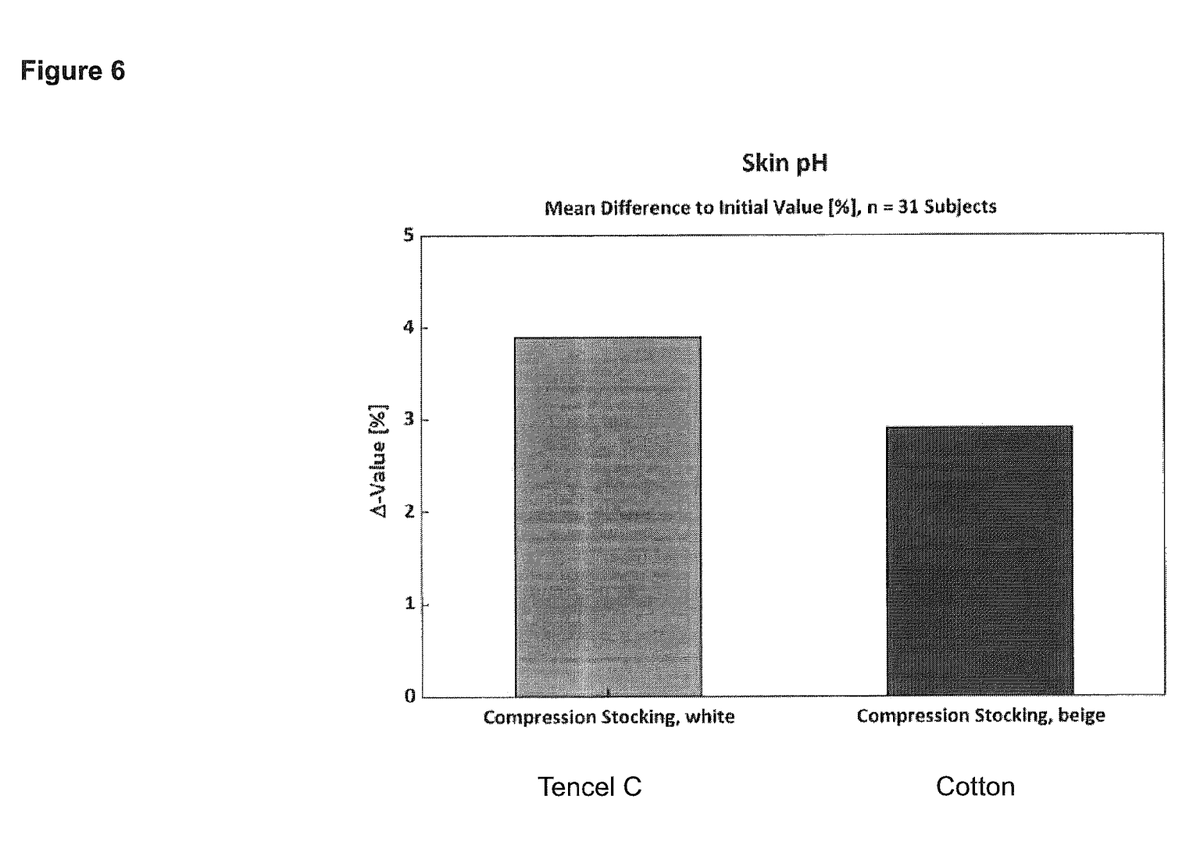

Results:

In FIG. 6, the Δ-deviation from the skin pH value before and after wearing Tencel C2 or cotton stockings is indicated. As can be seen from the Figure, there is almost no difference in pH value in case of Tencel C2-treated skin and cotton-treated skin.

EXAMPLE 6

Test of skin trophy, skin microclimate and wearing comfort of Tencel C2 containing stockings in comparison to conventional cotton stockings.

Test Performance 12 healthy test persons wore the Tencel C2 (chitosan) medical compression stocking on one leg and the cotton-containing comparison stocking on the other leg. The test persons completed a defined physical stress on the treadmill (treadmill ergometry). In connection with the treadmill ergometry, different measurements regarding the skin climate and the evaluation of the skin barrier function, e.g. a measurement of the skin moisture, evaporation of water, and skin temperature, were carried out.

All experiments were carried out in an air-conditioned testing room (20-24° C., average humidity of 60%). The test persons first of all completed a 20-minute acclimatization phase. The test persons walked 15 minutes on the treadmill at a speed of 3 km/h and a slope of 12°.

The abbreviations 1 to 5 used below refer to the respective examination times:

U1: before treadmill, without stocking
U2: before treadmill, with stocking
U3: after treadmill, with stocking
U4: after treadmill, without stocking
U5: 5 minutes after treadmill, without stocking.

Transepidermal Water Loss (TEWL, Courage and Khazaka, Cologne)

The transepidermal water loss (TEWL) provides information regarding the skin permeability and its barrier function. TEWL was measured using a Tewameter TM300 (Courage and Khazaka) as described above.

The obtained TEWL values are summarised in Table 3.

TABLE 3

Describing statistic of the examined TEWL values

| Stocking | Size | U1 | U2 | U3 | U4 | U5 |
|---|---|---|---|---|---|---|
| Cotton | Minimum | 2.40 | 2.30 | 7.00 | 9.30 | 7.00 |
|  | l.q. | 4.70 | 5.98 | 14.38 | 17.45 | 9.05 |
|  | Median | 6.75 | 7.85 | 19.10 | 28.05 | 13.95 |
|  | u.q. | 9.23 | 11.40 | 24.28 | 38.40 | 25.25 |
|  | Maximum | 10.00 | 16.60 | 34.90 | 55.20 | 37.30 |
| Tencel C | Minimum | 4.20 | 3.30 | 11.40 | 9.90 | 6.70 |
|  | l.q. | 5.18 | 6.28 | 13.53 | 24.38 | 8.10 |
|  | Median | 8.20 | 10.55 | 18.45 | 30.80 | 13.25 |
|  | u.q. | 11.88 | 14.00 | 20.23 | 38.40 | 23.50 |
|  | Maximum | 13.20 | 18.40 | 25.70 | 48.70 | 37.50 | l.q. = lower quartile;
u.q. = upper quartile

Figure 7:
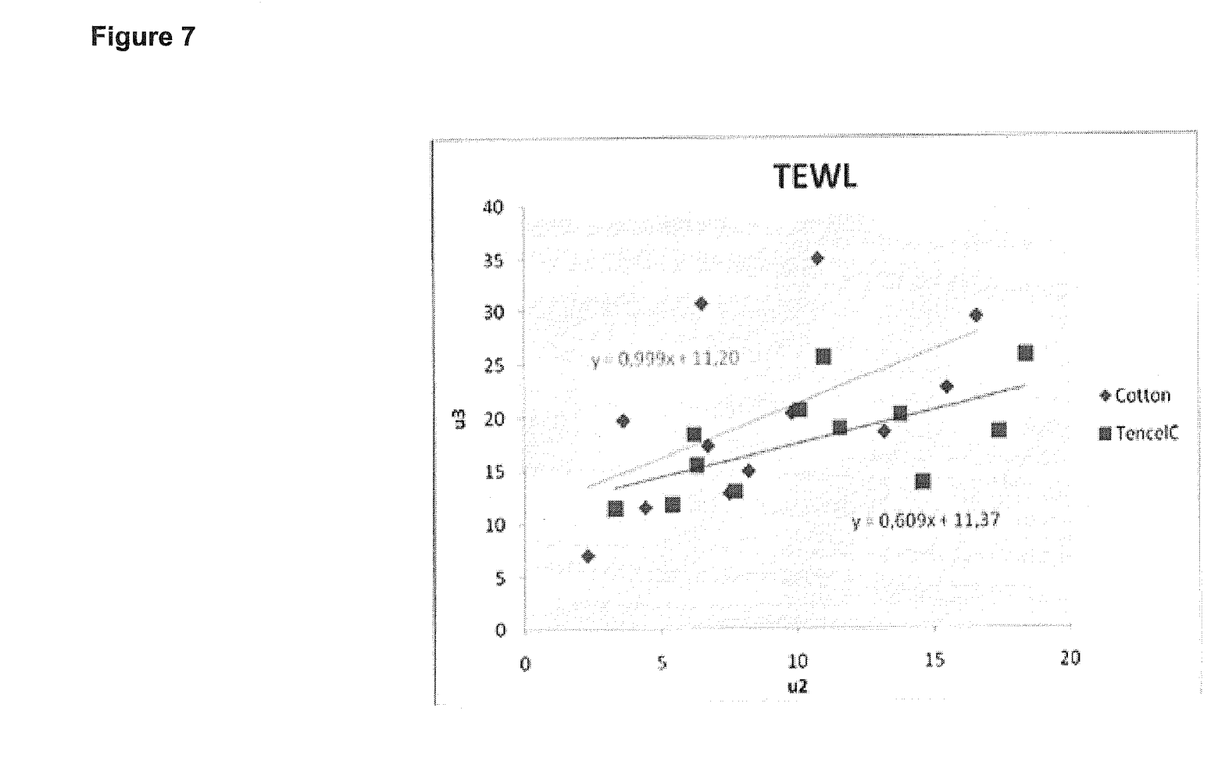

FIG. 7 shows a correlation between the TEWL value U2 before treadmill treatment and the TEWL value U3 after treadmill treatment. FIG. 7 indicates that the physical stress caused by treadmill treatment results in increased perspiration (perspiratio sensibilis) and an increased TEWL value in case of both compression stockings.

There is a higher increase of the TEWL value for the cotton stockings than for the Tencel C stockings. This can be explained by the fact that Tencel C can partially absorb and retain moisture such that the water vapour emission measured at the outer surface of the compression stocking is lower in Tencel C2 stockings as compared to cotton stockings.

Measurement of the Skin Moisture (Corneometry, Courage and Khazaka, Cologne)

The moisture content of the stratum corneum is measured via corneometry as described above. The stratum corneum is a suitable indicator due to its specific storage capacity.

The values for the skin moisture in the stratum corneum are shown in Table 4.

TABLE 4

| Skin moisture parameters | | | | |
|---|---|---|---|---|
| Stocking | Size | U1 | U4 | U5 |
| Cotton | Minimum | 33.40 | 31.50 | 34.80 |
| | l.q. | 38.95 | 42.85 | 43.00 |
| | Median | 41.00 | 45.65 | 45.05 |
| | u.q. | 47.33 | 56.00 | 50.53 |
| | Maximum | 56.10 | 60.30 | 57.30 |
| Tencel C | Minimum | 25.20 | 32.30 | 34.40 |
| | l.q. | 38.38 | 43.83 | 40.83 |
| | Median | 40.65 | 45.05 | 43.50 |
| | u.q. | 44.63 | 51.98 | 52.03 |
| | Maximum | 49.90 | 57.20 | 59.80 |

A correlation between U1 and U4 shows that an increase in skin moisture is observed in both types of stockings, However, the increase of the skin moisture is lower when wearing Tencel C2 stockings than when wearing cotton stockings.

When comparing the values measured at the time points U1 and U5, a similar result is obtained.

The corneometry data, thus, confirm the result of the TEWL measurements that Tencel C tends to cause less perspiration/skin moisture.

Temperature

The sensors were applied onto the skin, below the stocking. The measured temperatures are shown in Table 5.

Figure 8:
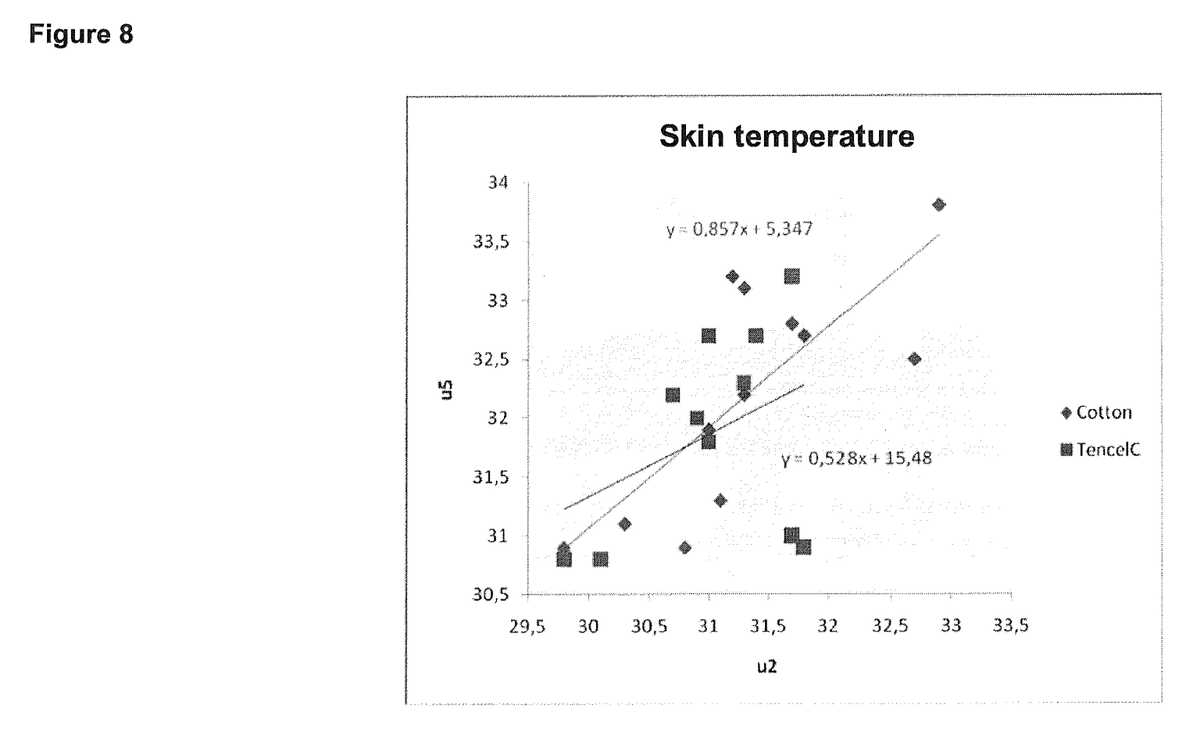

In FIG. 8, the relationship between U2 and U5 is schemattically displayed. Therein the slope of temperature increase is lower when wearing Tencel C2 stockings compared to the temperature increase when wearing cotton stockings.

The lower increase of the body temperature when wearing Tencel C2 stockings correlates with the lower TEWL value and the lower moisture increase (FIG. 8).

TABLE 5

| Describing statistic of the temperature parameters | | | | | | |
|---|---|---|---|---|---|---|
| Stocking | Size | U1 | U2 | U3 | U4 | U5 |
| Cotton | Minimum | 30.3 | 29.8 | 29.8 | 30.8 | 30.9 |
| | l.q. | 30.6 | 30.95 | 30.78 | 31.2 | 31.25 |
| | Median | 31.3 | 31.25 | 31.95 | 31.8 | 32.35 |
| | u.q. | 31.7 | 31.73 | 32.63 | 32.33 | 32.88 |
| | Maximum | 32.7 | 32.9 | 33.4 | 34.1 | 33.8 |
| Tencel C | Minimum | 29.8 | 29.8 | 29.8 | 30.6 | 30.8 |
| | l.q. | 30.73 | 30.85 | 30.75 | 31.25 | 30.98 |
| | Median | 31.1 | 31.15 | 32 | 31.75 | 32.1 |
| | u.q. | 31.63 | 31.48 | 32.23 | 32.33 | 32.4 |
| | Maximum | 31.8 | 31.8 | 32.7 | 32.8 | 33.2 |

Gravimetric Examination

The weight of the medical compression stockings has been determined before and after the treadmill treatment. The measurements have been carried out in closed plastic bags (to avoid moisture loss by evaporation) and by means of highly precise laboratory scales.

Figure 9:
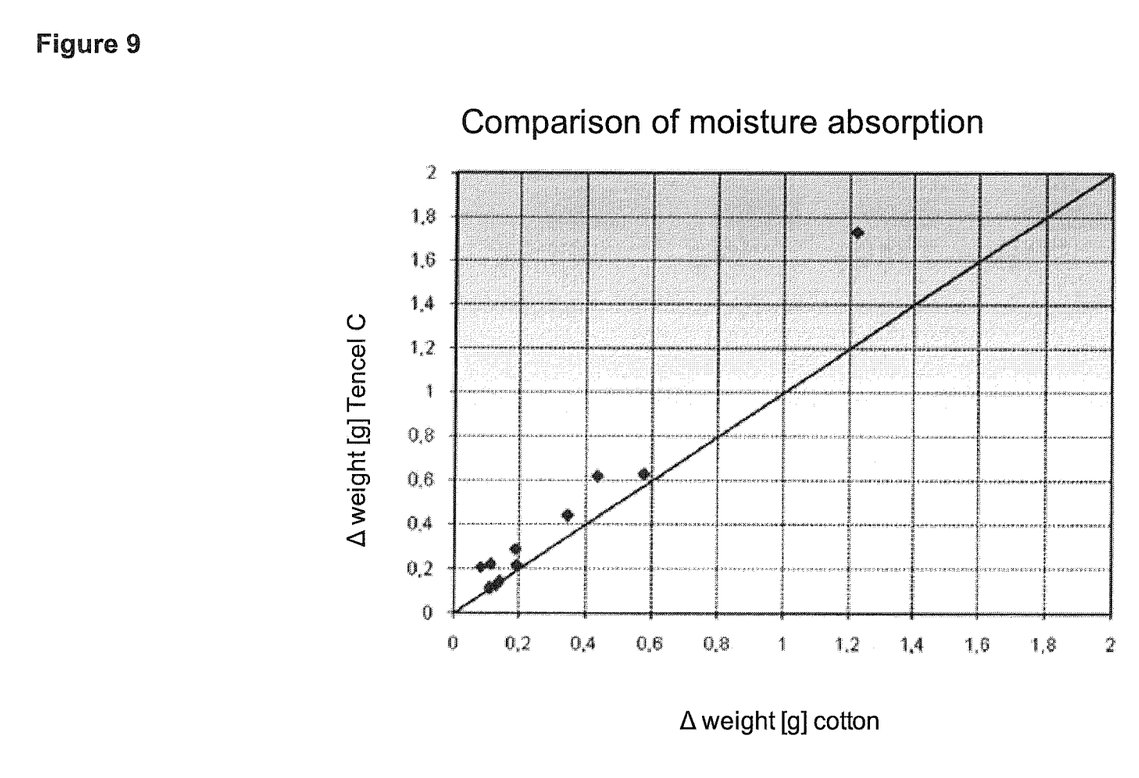

In FIG. 9, a correlation between the moisture increase of the Tencel C2 stockings ($\Delta$weight) and conventional cotton stockings after physical stress (treadmill) is shown. There is a clear deviation from the diagonal ($\Delta$weight tencel=$\Delta$weight cotton) suggesting that Tencel C absorbes more moisture.

The invention claimed is:

1. A compression garment comprising at least one fiber coated with chitosan, wherein the fiber is a cellulose-based fiber selected from the group consisting of viscose, modal, polynosic and lyocell fiber, wherein the surface of said fiber is at least partially coated with chitosan, and wherein said fiber coated with chitosan is spun onto an elastic yarn.

2. The compression garment according to claim 1, wherein said garment is selected from the group consisting of a stocking, arm sleeve, calf sleeve, glove, sock, leggings, top and shorts.

3. The compression garment according to claim 1, wherein said garment is capable of compression suitable for a medical garment.

4. The compression garment according to claim 3, wherein said compression is sufficient for phlebologic or lymphologic applications, for scar formation reduction or for diabetes patients.

5. The compression garment according to claim 1, wherein said garment is capable of compression suitable for wellness or sport applications.

6. The compression garment according to claim 1, wherein the fiber has a content of 0.1-25% by weight of chitosan.

7. The compression garment according to claim 1, wherein at least one fiber which is coated with chitosan covers an elastic yarn.

8. The compression garment according to claim 7, wherein the elastic yarn is selected from the group consisting of a synthetic yarn, a spandex yarn, and a natural elastic yarn.

9. The compression garment according to claim 8, wherein said synthetic yarn is made of a polyester-polyurethane copolymer, or said natural elastic yarn is made of rubber.

10. The compression garment according to claim 1, wherein the at least partially chitosan-coated fiber is blended with a further component selected from the group consisting of bamboo, wool, cotton, linen, silk, polyamide, polyester, polyacrylnitrile, polypropylene, viscose, modal, micro modal with elastane and elastodien.

11. The compression garment according to claim 10, wherein the amount of the at least partially chitosan-coated fiber in the blend is at least 3% by weight, based on the total-weight of the blend.

12. The compression garment according to claim 11, where the amount of the at least partially chitosan-coated fiber in the blend is at least 10% by weight, based on the total-weight of the blend.

13. The compression garment according to claim 12, where the amount of the at least partially chitosan-coated fiber in the blend is at least 20% by weight, based on the total-weight of the blend.

14. The compression garment according to claim 13, where the amount of the at least partially chitosan-coated fiber in the blend is at least 30% by weight, based on the total-weight of the blend.

15. The compression garment according to claim 14, where the amount of the at least partially chitosan-coated fiber in the blend is at least 40% by weight, based on the total-weight of the blend.

16. The compression garment according to claim 15, where the amount of the at least partially chitosan-coated fiber in the blend is at least 50% by weight, based on the total-weight of the blend.

17. A method for improving microbial skin flora, comprising applying a compression garment according to claim 1 to a subject in need of such improvement.

18. A method for improving compliance and wearing comfort of medical garments comprising applying a compression garment according to claim 1 to a subject in need of such improvement in compliance and wearing comfort.

19. A method for improving the regulation of skin moisture, comprising applying a compression garment according to claim 1 to a subject in need of such improvement in the regulation of skin moisture.

20. The method according to claim 18, wherein said compression garment is applied as an under-article which is in direct contact with the skin.

21. The method according to claim 20, wherein said under-article is selected from the group consisting of socks, stockings, knee socks, and tights.

22. A method for treating and/or preventing oedema in patients suffering from diabetes comprising applying a compression garment according to claim 1 to a subject in need of such treatment or prevention.

23. A method for improving skin thermoregulation, comprising applying a compression garment according to claim 1 to a subject in need of such improvement in skin thermoregulation.

24. A method for improving skin healing and protection, comprising applying a compression garment according to claim 1 to a subject in need of such improvement in skin healing and protection.

25. The method according to claim 18, where said subject is suffering from aging, sensitive and/or dry skin.

26. The compression garment according to claim 1, wherein said fiber coated with chitosan is spun onto an elastic yarn by wrap spinning.

\* \* \* \* \*